US007186698B2

(12) United States Patent
Moonen

(10) Patent No.: US 7,186,698 B2
(45) Date of Patent: Mar. 6, 2007

(54) SPATIAL AND TEMPORAL CONTROL OF GENE EXPRESSION USING A HEAT SHOCK PROTEIN PROMOTER IN COMBINATION WITH LOCAL HEAT

(75) Inventor: Chrit Moonen, Bordeaux (FR)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 344 days.

(21) Appl. No.: 10/096,549

(22) Filed: Mar. 11, 2002

(65) Prior Publication Data
US 2002/0165191 A1  Nov. 7, 2002

Related U.S. Application Data

(63) Continuation of application No. 09/242,244, filed as application No. PCT/US97/15270 on Aug. 14, 1997, now abandoned.

(60) Provisional application No. 60/024,213, filed on Aug. 15, 1996.

(51) Int. Cl.
*A01N 43/04* (2006.01)
*A61K 31/70* (2006.01)
*C07H 21/02* (2006.01)
*C07H 21/04* (2006.01)

(52) U.S. Cl. .................. 514/44; 536/23.1; 536/24.1
(58) Field of Classification Search ............... 514/44; 536/23.1, 24.1; 435/325; 800/8
See application file for complete search history.

(56) References Cited

U.S. PATENT DOCUMENTS 5,490,840 A   2/1996  Uzgiris et al.
5,521,084 A   5/1996  Kowalski et al.

FOREIGN PATENT DOCUMENTS

| EP | 0 118 393 A2 | 9/1984 |
|---|---|---|
| EP | 0 263 908 A1 | 4/1988 |
| EP | 0 299 127 A1 | 1/1989 |
| EP | 0 336 523 A1 | 10/1989 |
| WO | WO 87/00861 A1 | 2/1987 |
| WO | WO 87/04727 A1 | 8/1987 |
| WO | WO 87/05935 A1 | 10/1987 |
| WO | WO 90/01543 A1 | 2/1990 |
| WO | WO 90/11092 A | 10/1990 |
| WO | WO 95/00178 A1 | 1/1995 |
| WO | WO 95/03418 A2 | 2/1995 |

OTHER PUBLICATIONS

Angles, J. M. et al., "Effects of pulsed ultrasound and temperature on the development of rat embryos in culture" *Teratology*, vol. 42; pp. 285-293 (1990).

Burdon, R. H., "Heat shock proteins in relation to medicine", *Molec. Aspects Med.*, vol. 14; pp. 83-165 (1993).
Cline, H. E. et al., "Focused US system for MRI imaging-guided tumor ablation" *Radiology*, vol. 194; pp. 731-737 (1995).
Voellmy, R., "Transduction of the stress signal and mechanisms of transcriptional regulation of heat shock/stress protein gene expression in higher eukaryotes" Crit. Rev. Eukar. Gene Expr., vol. 4, No. 4; pp. 357-401 (1994).
de Zwvart, J. A. et al., "Ultra fast MRI thermometry" Abstract for Scientific Presentation at the Society of Magnetic Resonance 4th Scientific Meeting, New York, NY, Apr. 27-May 3, 1996.
de Zwart, J. A. et al., "Fast magnetic-resonance temperature imaging" J. Magnetic Resonance, Ser. B-112, Art. No. 0115, pp. 86-90 (1996).
Amin, H. et al.: "Organization of the *Drosophila melanogaster* hsp70 heat shock regulation unit" *Mol. Cell. Biol.*; Mar. 1987; pp. 1055-1062.
Anderson, W. F.: "Human gene therapy" *Nature*; vol. 392; Apr. 30, 1998; pp. 25-30.
Crystal, R. G.: "Transfer of genes to humans: Early lessons and obstacles to success" *Science*; vol. 270; Oct. 20, 1995; pp. 404-410.
Dreano, M. et al.: "High-level, heat-regulated synthesis of proteins in eukaryotic cells" *Gene*; vol. 49; 1986; pp. 1-8.
Dreano, M. et al.: Production of secretable proteins using the passage in vivo as tumours of cells carrying heat-inducible expression constructs *Biotechnology*; vol. 6, Aug. 1988; pp. 953-958.
Fan, X. and K. Hynynen: "Control of the necrossed tissue volume during noninvasive ultrasound surgery using a 16-element phased array" *Med. Phys.*; vol. 22, No. 3; Mar. 1995; pp. 297-306.
Hynynen et al.: "MRI-guided noninvasive ultrasound surgery" *Med. Phys.*; vol. 20, No. 1; Jan./Feb. 1993; pp. 107-115.
Rancourt, E. et al.: "Flounder antifreeze protein synthesis under heat shock control in *Drosophila melanogaster*" *Mol. Cell. Biol.*; Jun. 1987; pp. 2188-2195.
Stedman's Medical Dictionary, Williams & Wilkins, 1995.
Verma et al.: "Gene therapy—promises, problems and prospects" *Nature*; vol. 389; Sep. 18, 1997; pp. 239-242.
Craig, E.A. and C.A. Gross: "Is hsp70 the cellular thermometer?" *Trends Bioch. Sci.* vol. 16; pp. 135 (1991).
Dreano, M. et al. (1998) "Antibody formation against heat-induced gene products expressed in animals" *Bio/Technology* vol. 6, No. 11; pp. 1340-1343.
Hightower, L.E.: "Heat shock, stress proteins, chaperones and proteotoxicity" *Cell*, vol. 66; pp. 191-197 (1991).
Holbrook, N.J. and Udelsman: "Heat shock protein gene expression in response to physiological stress and aging," in The Biology of Heat Shock Proteins and Molecular Chaperones (Morimoto et al. eds., Plainview, NY: Cold Spring Harbor Laboratory Press, pp. 577-593) (1994).

(Continued)

Primary Examiner—Joseph Woitach
(74) Attorney, Agent, or Firm—Klarquist Sparkman, LLP

(57) ABSTRACT

The invention provides methods for using local heat to control gene expression. The heat shock protein (hsp) gene promoter is recombined with a selected therapeutic gene and expressed in selected cells. Local controlled heating is used to activate the hsp promoter, for example by using focused ultrasound controlled by MRI.

6 Claims, 5 Drawing Sheets

OTHER PUBLICATIONS

Hunt, C. and R.I. Morimoto: "Conserved features of eukaryotic hsp70 genes revealed by comparison with the nucleotide sequence of human hsp70" *Proc. Natl. Acad. Sci. USA*; vol. 82., pp. 6455-6459 (1985).

Kay, R. J. et al.: "Expression of intron-containing *C. elegans* heat shock genes in mouse cells demonstrates divergence of 3'splice site recognition between nematodes and vertebrates, and an inhibitory effect of heat shock on the mammalian splicing apparatus" *Nucl. Acids Res.*; Vo. 15, No. 9; pp. 3723-3741 (1987).

Lis, J. and C. Wu: "Protein traffic on the heat shock promoter: Parking, stalling, and trucking along" *Cell*; vol. 74; pp. 1-4 (1993).

Macario, (1995), "Heat-shock proteins and molecular chaperones: Implications for pathogenesis, diagnostics, and therapeutics," *Int. J. Chem. Lab Res.* vol. 25; pp. 59-70 (1995).

Miller, M.W. and M.C. Ziskin: "Biological consequences of hyperthermia" *Ultrasound Med. Biol.* vol. 15, No. 8; pp. 707-722 (1989).

Miller, A.D.: "Human gene therapy comes of age" *Nature*; vol. 357; pp. 455-460 (1992).

Morimoto et al., eds., Stress Proteins in Biology and Medicine (1990) Cold Spring Harbor Press (1990) esp. Chapters 5 and 6 (pp. 101-130) and pp. 248-252; pp. 255-268.

Mulligan, R.C. "The basic science of gene therapy" *Science* vol. 260; pp. 926-932 (1993).

Samulski, T.V. et al.: "Non-invasive thermometry using magnetic resonance diffusion imaging: potential for application in hyperthermic oncology" *int. J. Hyperthermia*, vol. 8, No. 6, pp. 819-829 (1992).

Wu, B., et al. "Structure and expression of the human gene encoding major heat shock protein HSP70" *Mol. Cell. Biol.* vol. 5, No. 2: pp. 330-341 (1985).

Yost, H.J. and S. Lindquist: "RNA splicing is interrupted by heat shock and is rescued by heat shock protein synthesis" *Cell* vol. 45; pp. 185-193 (1986).

```
         -88        HSEII              -64      HSEI
       G CTCTCGTTGGTTC GAGAGA GCGC GCCTCGAATGTTCGCGAA AAGAGCGCCGG
         -33                                       41
       AG TATAAATA GAGGCGCTTCGTCTACGGAGCGAC A ATTCAATTCAAACAAGCAAA
```

FIG. 3A.

```
                    +18:+
                    +16:+
                    +14:-
                    +12:-                   +16:+++
                    +10:++                  +14:+++
                     +8:+++                 +11:+++
                     +6:+++ /               +10:+++
                     +4:-  /                 +8:+++
                     +3:-                    +6:+++
              HSEII  +2:-  /        -64 HSEI +4:+++ /   -33
       CTCTCGTTGGTTC GAGAG /     GCCTCGAATGTTCGCGAA  /     TATAAATA
       GCCTCGAATGTTCGCGAA
              HSEI      /+3:+++\
                       / +4:+++
                      /  +6:+++
                     /   +8:+++
                        +10:+++
                        +14:+++
                        +16:+++
                        +18:+++
```

FIG. 3B.

```
                                          -285
                                          GCGTCCTCAGAGCCA
       -270                               ●++
       GCCGGGAGGAG CTAGAACCTTCCCCGCGTTTC TTTCAGCAGCCCTGAGTCAGAGGCGG
       -212                                                 ●+
       GCTGGCCTTGCAAGTAGCCGCCCAGCCTTCTTCGGTCTCACGGACCGATCCG CCCGAA
       -154                                                       ●+
       CCTTCTCCCGGGGTC AGCGCCGCGCTGCGCCGCCCGGCTGACTCAGCCCGGGCGGGCG
       -96    ●-                                                ●-
       GGCGGGAGGCTCTCGACTGGG CGGGAAGGTGCGGGAAGGTTCGCG GCGGCGGGGTCGG
       -38                                 +1
       GGAGGTGC AAAAGGATGAAAA GCCCGTGGACGGAGCTGA
```

FIG. 3C.

```
LOCUS        HUMHSP70C      197 bp      DNA                PRI         01-SEP-1988
DEFINITION   Human 70k dalton heat shock protein promoter.
ACCESSION    M12690
NID          g184415
KEYWORDS     heat shock protein.
SOURCE       Homo sapiens DNA.
  ORGANISM   Homo sapiens
             Eukaryotae; mitochondrial eukaryotes; Metazoa; Chordata;
             Vertebrata; Eutheria; Primates; Catarrhini; Hominidae; Homo.
REFERENCE    1  (bases 1 to 197)
  AUTHORS    Wu,B.J., Kingston,R.E. and Morimoto,R.I.
  TITLE      Human HSP70 promoter contains at least two distinct regulatory
             domains
  JOURNAL    Proc. Natl. Acad. Sci. U.S.A. 83, 629-633 (1986)
  MEDLINE    86120994
FEATURES             Location/Qualifiers
     SOURCE          1..197
                     /organism="Homo sapiens"
BASE COUNT       44 a     48 c     73 g     32 t
ORIGIN
        1 gaagagtctg gagagttctg agcaggggggc ggcactctgg cctctattgg tccaggaagg
       61 ctgggggca ggacgggagg ccaaaccct ggaatattcc cgacctggca gcctcatcga
      121 ggctcggtga ttggctcaga agggaaaagg cgggtctccg tgacgactta taaaacgcca
      181 ggggcaacgg gtccgga
```

FIG. 4.

SPATIAL AND TEMPORAL CONTROL OF GENE EXPRESSION USING A HEAT SHOCK PROTEIN PROMOTER IN COMBINATION WITH LOCAL HEAT

CROSS REFERENCES TO RELATED APPLICATION

This application is a continuation application claiming benefit under 35 U.S.C. §120 of U.S. patent application Ser. No. 09/242,244, filed on Feb. 29, 2000, now abandoned which is the National Stage of International Application No. PCT/US597/15270, filed on Aug. 14, 1997, which claims the benefit of the U.S. Provisional Patent Application No. 60/024,213, filed on Aug. 15, 1996, the contents of which are herein incorporated by reference in their entirety.

BACKGROUND OF THE INVENTION

A. Field of the Invention

The present invention relates to the spatial and temporal control of exogenous gene expression in genetically engineered cells and organisms. In particular, the invention relates to the use of heat-inducible promoters such as the promoter of heat shock genes to control the expression of exogenous genes. More particularly, the invention relates to the use of focused ultrasound to heat cells that contain therapeutic genes under the control of a heat shock promoter, thereby inducing the expression of the therapeutic gene.

B. Description of Related Art

Disorders caused by a malfunctioning gene can-be treated by stably transferring an exogenous functional gene into a host cell, so that the gene product of that gene is produced in the host cell. Gene transfer may also be used to express in a host cell exogenous nucleic acids that kill the host cell, or that encode gene products that alter the phenotype of the host cell and/or the metabolic state of surrounding cells, or that suppress the expression of selected genes in the host cell. Human diseases are amenable to treatment by this approach, particularly those diseases where the defect is with a single gene. For discussions on the application of gene therapy towards the treatment of genetic as well as acquired diseases See Miller, A. D. (1992) *Nature* 357: 455–460, and Mulligan, R. C. (1993) *Science* 260:926–932, both incorporated herein by reference.

In many instances, it is desirable to express genetically engineered genes only in certain tissues, and/or at will only at certain times, and/or only to a certain degree. However, current gene transfer and exogenous gene expression protocols do not provide adequate means of simultaneously controlling which cells in a heterogeneous population are transformed, and when, where and to what degree the transferred genes are expressed.

One approach for the control of exogenous gene expression that has received a great deal of attention is to transform host cells with a gene that is under the control of an inducible promoter, and then to switch the transferred gene on and off at will by activating the inducible promoter. Inducible promoters include: the metallothionine IIA promoter, the lacZ, tac, and trp promoters, the phage T7 promoter/T7 RNA polymerase, the *Candida albicans* MAL2 gene promoter. Some promoters are heat inducible: e.g., the lambda PL promoter with a C1857 repressor, heat shock protein promoters.

Heat shock proteins ("hsps") are a ubiquitous class of proteins produced in response to stress, notably heat stress, as well as a variety of other external agents. All cells that have so far been tested contain-hsps, and many different hsps have been identified in a wide range of organisms. Many hsps are designated according to their molecular mass, (e.g. hsp70 refers to a 70 kDalton hsp; hsp56, hsp28). Additional examples of hsps include ubiquitin, crystallin, rapamycin, P-glycoprotein, and others. The following articles describe the properties of heat shock genes and promoters: Yost et al., (1990) *TIG*, 6:222–226. RNA metabolism: strategies for regulation in the heat shock response. Pennier, (1994) *Biochemie,* 76:737–747. Translational control during heat shock; Minowada and Welch, (1995) "The Clinical implications of the stress response", *J. Clin. Invest.* 95:3–12; Lis and Wu, (1993) *Cell* 74:1–4. Protein traffic on the heat shock promoter: parking, stalling, and trucking along; Holbrook and Udelsman, "Heat shock protein gene expression in response to physiological stress and aging," in THE BIOLOGY OF HEAT SHOCK PROTEINS AND MOLECULAR CHAPERONES" (Morimoto et al., (1994) Editors, Plainview, N.Y.: Cold Spring Harbor Laboratory Press, pp. 577–593); Macario, (1995), "Heat-shock proteins and molecular chaperones: implications for pathogenesis, diagnostics, and therapeutics," *Int. J. Chem. Lab Res.* 25:59–70.

Hsps participate in and influence a large variety of cellular effects, including the assembly of newly formed polypeptides (some HSPs function as chaperones), signalling functions (e.g. response to steroid hormones), protein excretion, DNA and RNA synthesis (see below). The synthesis of proteins during heat shock is generally inhibited during stress, except for the synthesis of the hsps.

Heat shock (and other forms of stress) result in the almost immediate transcriptional activation of heat shock genes. The heat shock response is quite dramatic. The heat shock messages appear in the cytoplasm generally within minutes, and the translation of message is carried out with a very high efficiency. For example, in Drosophila cells, hsp genes are induced within just four minutes after a temperature elevation of 4 to 9° C. Within one hour, there are several thousand transcripts per cell. These transcripts are actively translated into hsp while at-the same time, the transcription of previously active genes is severely repressed. Miller and Ziskin (1990) *Ultrasound Med. Biol.* 15:707–22 reported that short exposures to sharply elevated temperature result in a protective effect against further thermal insult, and that the generation of heat shock proteins by cells coincides with the onset of such "thermal protection. "The level of synthesis of hsp70 in cells during heat shock appears to be linearly related to their thermotolerance. Li, G. C. (1985) *Int. J. Radiat. Oncol. Biol. Phys.* 11:165–177. Two human hsp70 proteins have been described-hsp70A (Wu, B., et al. (1985) *Mol. Cell. Biol.* 5:330–341; Hunt, C., and Morimoto, R. I. (1985) *Proc. Natl. Acad. Sci. USA* 82.: 6455–6459) and hsp70B (Schiller, P., et al. (1988) *J. Mol. Biol.* 203:97–105). For a review of hsps, see, e.g., Morimoto et al., eds., *Stress Proteins in Biology and Medicine (*1990) Cold Spring Harbor Press; Hightower, L. E. (1991) *Cell* 66:191–197.; Craig, E. A., and Gross, C. A. (1991) *Trends Bioch. Sci.* 16:135.

The heat shock genes of many organisms have been mapped and sequenced. Heat shock genes are scattered at various chromosomal locations. A remarkable feature of these genes is the general absence of any intervening sequences.

Heat shock promoters from different sources have been have been isolated, sequenced and used to express a variety of genes. For example, Dreano, M., et al. (1986) *Gene* 49:1–8, describe the use of the human hsp70B promoter, as well as a *Drosophila* hsp70 promoter, to direct the heat regulated synthesis of human growth hormone, chicken lysozyme and a human influenza hemagglutinin. EPA Publication No. 336,523 (Dreano et al., published 11 Oct. 1989) describes the in vivo expression of human growth hormone using a human hsp70 promoter. PCT Publication No. WO 87/00861 (Bromley et al., published 12 Feb. 1987) describes the use of human and *Drosophila* hsp promoters having 5'-untranslated region variants. EPA Publication No. 118, 393 (Bromley et al., published 12 Sep. 1984) and PCT Publication No. WO 87/05935 (Bromley et al., published 8 Oct. 1987) describe the expression of *E. coli* beta-galactosidase and human influenza hemagglutinin, using a *Drosophila* hsp70 promoter. See also U.S. Pat. Nos. 4,990,607, 4,797,359, 5,521,084, and 5,447,858. Overexpression of hsp-70 has been accomplished in transgenic mice. Plumeer et al., (1995) *J. Clin. Inv.* 95:1854–1860. See also Yost and Lindquist, (1986) *Cell* 45:185–193, Yost and Lindquist, (1988) *Science* 242:1544–1548, Garbe et al. (1986) *PNAS,* 83:1812–1816, Blackman et al. (1986) *J. Mol. Biol.* 188: 499–515, Bond et al. (1986) *Mol. Cell. Biol.* 12:4602–4610, Kay et al. (1987) *Nucl. Acids Res.* 15:3723–3741, Bond, (1988) *EMBO J.* 7:3509–3518. The published sequences of these promoters are hereby incorporated by reference.

The inducible promoter systems which have been used to control the expression of proteins typically have one or more of the following limitations: they are restricted to a relatively narrow range of host cells, or are only partially inducible, or are derived from organisms, such as tumor viruses, which are inherently dangerous.

More importantly, their use does not allow for finely tuned localized expression of exogenous genes in transformed cells. "Among the design hurdles for all vectors are . . . to enable the transferred gene to be regulated". Crystal (1995), "Transfer of genes to humans: Early lessons and obstacles to success."

SUMMARY OF THE INVENTION

The present invention provides a method for selective temporal and spatial control of gene expression, comprising the steps of:
a) linking a therapeutic gene with a heat shock protein promoter to yield a genetically engineered construct in which the selected therapeutic gene is under the control of the hsp promoter;
b) inserting the hsp promoter-therapeutic gene construct into a suitable vector and introducing the vector into a target cell or organism,
c) selectively heating a predetermined discrete region of a cell mass or organism that includes cells that contain the vector construct,
d) repeating step c as many times as necessary.

In a preferred embodiment, the local heating is accomplished using focused ultrasound. A magnetic resonance imaging instrument is used to visualize the target tissue and to quantify and finely control the level of heating (i.e., temperature).

The invention also supplies a method of providing a therapeutic protein to selected cells in a multicellular organism, comprising:
introducing into cells of a multicellular organism a DNA molecule having a heat shock promoter sequence operably linked to and exerting regulatory control over a sequence encoding a therapeutic protein, and
activating said heat shock promoter sequence through the application of a focused ultrasound so that said cells express a therapeutically effective amount of said therapeutic protein.

In a number of embodiments, the invention comprises methods of treating cancer, to induce local angiogenesis, and to treat genetic diseases. In some embodiments, the gene of interest is selected from the group of genes that encode toxic molecules or pro-molecules.

BRIEF DESCRIPTION OF THE FIGURES

FIG. 3 depicts an hsp promoter. FIGS. 3A and 3B depict a minimal *Drosophila* hsp70 promoter containing HSEII, HSEI, GAGA and TATA elements. +1 refers to the transcription start site. FIG. 3C depicts the nucleotide sequence of the human hsp70B promoter.

FIG. 4 depicts a human hsp promoter obtained from the Genbank database (SEQ ID NO:5).

FIG. 5(*b*) is a temperature change map for the same slice after one minute of heating.

FIG. 5(*c*) depticts the temperature change after three minutes of heating. Thermal diffusion is apparent. This state was maintained throughout the 45 minute heating interval. Temperature images were obtained during FUS application.

DETAILED DESCRIPTION OF THE INVENTION

A. Definitions

Figure 1:
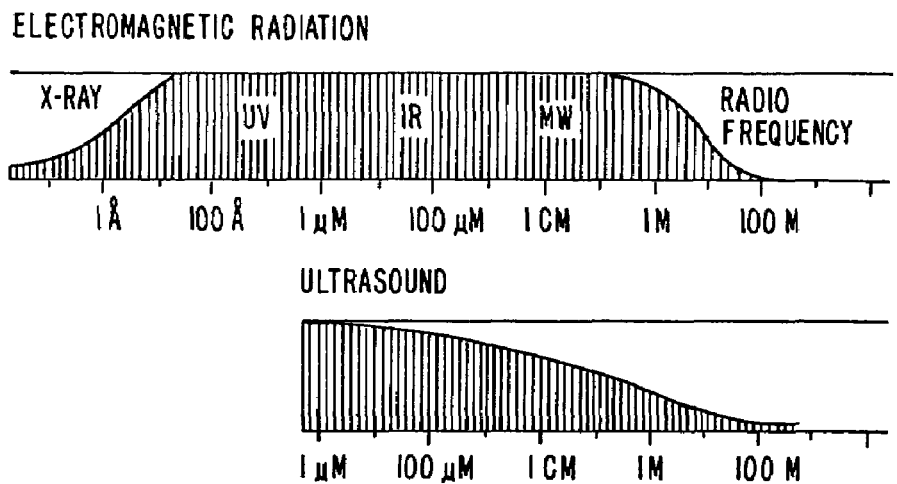
FIG. 1 is a graph of attenuation of radiation by human tissue.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. The term nucleic acid is used interchangeably with gene, cDNA, and MRNA encoded by a gene.

The phrase "exogenous" or "heterologous nucleic acid" generally denotes a nucleic acid that has been isolated, cloned and ligated to a nucleic acid with which it is not combined in nature, and/or introduced into and/or expressed in a cell or cellular environment other than the cell or cellular environment in which said nucleic acid or protein may typically be found in nature. The term encompasses both nucleic acids originally obtained from a different organism or cell type than the cell type in which it is expressed, and also nucleic acids that are obtained from the same cell line as the cell line in which it is expressed.

The phrase "a nucleic acid sequence encoding" refers to a nucleic acid which contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences which may be introduced to conform with codon preference in a specific host cell.

The term "recombinant" or "engineered" when used with reference to a nucleic acid or a protein generally denotes that the composition or primary sequence of said nucleic acid or protein has been altered from the naturally occurring sequence using experimental manipulations well known to those skilled in the art. It may also denote that a nucleic acid or protein has been isolated and cloned into a vector, or a nucleic acid that has been introduced into or expressed in a cell or cellular environment other than the cell or cellular environment in which said nucleic acid or protein may be found in nature.

The term "recombinant" or "engineered" when used with reference to a cell indicates that the cell replicates or expresses a nucleic acid, or produces a peptide or protein encoded by a nucleic acid, whose origin is exogenous to the cell. Recombinant cells can express nucleic acids that are not found within the native (nonrecombinant) form of the cell. Recombinant cells can also express nucleic acids found in the native form of the cell wherein the nucleic acids are re-introduced into the cell by artificial means.

A cell has been "transformed" by an exogenous nucleic acid when such exogenous nucleic acid has been introduced inside the cell membrane. Exogenous DNA may or may not be integrated (covalently linked) into chromosomal DNA making up the genome of the cell. The exogenous DNA may be maintained on an episomal element, such as a plasmid. In eucaryotic cells, a stably transformed cell is generally one in which the exogenous DNA has become integrated into the chromosome so that it is inherited by daughter cells through chromosome replication, or one which includes stably maintained extrachromosomal plasmids. This stability is demonstrated by the ability of the eucaryotic cell to establish cell lines or clones comprised of a population of daughter cells containing the exogenous DNA.

"Heat-inducible promoter." A promoter is a nucleic acid sequence associated with a gene that controls the transcription of the gene by interacting with mainly transacting ligands such as polymerases, transcription factors, transcription enhancers and transcription suppressors. Promoters can be either constitutive or inducible. A constitutive promoter promotes the constant transcription of a gene, whereas an inducible promoter's activity fluctuates as determined by the presence (or absence) of a specific inducer. The regulatory elements of an inducible promoter are usually located further upstream of the transcriptional start site than the TATA box. Ideally, an inducible promoter should possess the following properties: a low to nonexistent basal level of expression in the absence of inductive stimulus, a high level of expression in the presence of inductive stimulus, and an induction scheme that does not otherwise alter the physiology of the cell. A heat inducible promoter is one that is activated by exposing cells that contain the is promoter to a defined temperature increase.

A "host cell" is a cell which has been transformed by an exogenous DNA sequence. Unless otherwise specified, the host cell may be a plant or animal cell.

The term "tumor cell" or "cancer cell" or "neoplastic cell" denotes a cell that demonstrates inappropriate, unregulated proliferation. A "human" tumor is comprised of cells that have human chromosomes. Such tumors include those in a human patient, and tumors resulting from the introduction into a nonhuman host animal of a malignant cell line having human chromosomes into a nonhuman host animal.

"Selectively heating" means that only cells having predetermined spatial coordinates in an organism, tissue or cell mass are directly heated by the heat source, whereas cells that are outside of these coordinates, even though adjacent, are not directly heated. Heating of adjacent cells that may occur by normal heat equilibration between the selectively heated cells and the adjacent cells is a consequence of selective heating.

The term "pro-molecule" refers to a substance that is itself not metabolically active as administered, but that is activated either when chemically altered or metabolized by cells capable of altering or metabolizing the pro-molecule, or when combined with one or more other substances to form a complex that is metabolically active. A pro-molecule may, upon chemical alteration or combination with a second substance, become toxic to the host cell. Examples include 5-fluorocytosine ("5FC"), which can be converted to the lethal metabolite 5-fluorouracil ("5FU"); 5-methoxypurine arabinoside; and gancyclovir. Pro-molecules preferably cause no substantially no ill effects to an organism except to cells that are capable of converting the pro-drug to a toxic product (i.e., metabolite or complex). "Pro-drug activating molecule" denotes a molecule such as an enzyme that is capable of metabolizing the non-toxic pro-drug to its toxic metabolite, or a molecule that combines (covalently or non-covalently) with a pro-drug to yield a toxic product.

A "toxic molecule" is a molecule that inhibits cell growth, or inhibits certain metabolic pathways, in some instances killing the cell. See, e.g., WO 93/24136.

The phrase "therapeutic dose" or "therapeutic amount" or "effective amount" means a dosage sufficient to produce a desired result. The desired result can be subjective or objective improvement in the recipient of the dosage, a decrease or an increase in the number of a target population of cells, a decrease in tumor size, a decrease in the rate of growth of cancer cells, a decrease in metastasis, or any combination of the above.

B. The Invention

In accordance with the present invention, a nucleic acid comprising a heat-inducible promoter, preferably an hsp promoter, is obtained, coupled by known genetic engineering techniques to a selected gene, the construct is introduced into host cells, and a subset of transformed cells that occupy selected spatial coordinates are heated to activate the promoter and express the gene.

1. Heat Shock Proteins and Heat Shock Protein Promoters

A number of heat inducible promoters are known (e.g., the lambda PL promoter; and may be used herein. The preferred heat inducible promoter for use in the present invention is a heat shock protein promoter.

A region known as the heat shock element (HSE), is found within the first 100 bp 5' of the RNA start site of eucaryotic heat shock genes. Sorger, P. K. (1991) *Cell* 65:363. This region includes the sequence nGAAn, repeated at least two times in head-to-head or tail-to-tail orientation (nGAAnnTTCn (SEQ ID NO:6) or nTTCnnGAAn (SEQ ID NO:7)). Hsp7O genes from different species differ in the number and orientation of HSEs and in the types of other factor-binding sites found upstream. The HSE functions in stress induced promoter activation by binding a positive transactivating factor, the heat shock factor (HSF). The binding constant of this factor to the heat shock element is about a hundred fold higher than that of any other known mammalian transcription factor to its respective binding site, rendering this promoter one of the strongest.

The primary site for the regulation of protein synthesis is the initiation of the polypeptide chain. In particular, the activity of elF-2, and elF-4F, both initiation factors, is modulated during heat shock. A hsp-related protein Idnase is thought to be involved in the regulation of initiation factors. Hsp-70 is thought to-be a heat sensor by detecting the accumulation of denatured proteins, and the production of eIF-2 is thought to limit protein production. In turn, the factor eIF-4F could be involved in the preferential synthesis of the hsps.

The specific transcription factor activated during heat shock is often referred to as HSF-1. Recent reviews summarize its action. HSP-1 trimerizes during stress (mediated by hsp-70) and then binds to a consensus nucleotide sequence (the heat shock element (HSE), located within the promoter element of the hsp genes.

Heat shock promoters not specifically described herein are nonetheless within the scope of the present invention if they meet the following criteria:

when recombined with a reporter gene to form a construct that is then introduced into a host cell that is capable of expressing the reporter gene, the reporter gene is minimally or not at all expressed at normal physiologic temperatures, but when the transformed host cell is exposed to non-lethal supraphysiological temperatures, the reporter gene is expressed at a level which is at least five times (preferably 10 times, and most preferably at least 100 times) the level of expression at physiological temperatures.

2. Genetic Engineering Methods for Obtaining a Heat Shock Promoter, Operably Linking it to a Selected Gene, and Expressing it in Cells.

In brief summary, the expression of natural or synthetic nucleic acids is typically achieved by operably linking a nucleic acid of interest to a promoter (which is either constitutive or inducible), incorporating the construct into an expression vector, and introducing the vector into a suitable host cell. Typical vectors contain transcription and translation terminators, transcription and translation initiation sequences, and promoters useful for regulation of the expression of the particular nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman and Smith (1979), *Gene*, 8:81–97; Roberts et al. (1987), *Nature*, 328:731–734; Berger and Kimmel, *Guide to Molecular Cloning Techniques, Methods in Enzymology*, volume 152, Academic Press, Inc., San Diego, Calif. (Berger); Sambrook et al. (1989), MOLECULAR CLONING—A LABORATORY MANUAL (2nd ed.) Vol. 1–3, Cold Spring Harbor Laboratory, Cold Spring Harbor Press, N.Y., (Sambrook); and F. M. Ausubel et al., CURRENT PROTOCOLS IN MOLECULAR BIOLOGY, eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.), as well as many other commercial sources known to one of skill.

a. Nucleic Acids

The nucleic acids (including, promoters, genes and vectors) used in the present method can be isolated from natural sources, obtained from such sources as ATCC or GenBank libraries, or prepared by synthetic methods. Synthetic nucleic acids can be prepared by a variety of solution or solid phase methods. Detailed descriptions of the procedures for solid phase synthesis of nucleic acids by phosphitetriester, phosphotriester, and H-phosphonate chemistries are widely available. See, for example, Itakura, U.S. Pat. No. 4,401,796; Caruthers, et al., U.S. Pat. Nos. 4,458,066 and 4,500,707; Beaucage, et al., (1981) *Tetrahedron Lett.*, 22:1859–1862; Matteucci, (1981) et al., *J. Am. Chem. Soc.*, 103:3185–3191; Caruthers, et al., (1982) *Genetic Engineering*, 4:1–17; Jones, chapter 2, Atkinson, et al., chapter 3, and Sproat, et al., chapter 4, in *Oligonucleotide Synthesis: A Practical Approach*, Gait (ed.), IRL Press, Washington D.C. (1984); Froehler, et al., (1986) *Tetrahedron Lett.*, 27:469-472; Froehler, et al., (1986) *Nucleic Acids Res.*, 14:5399-5407; Sinha, et al. (1983) *Tetrahedron Lett.*, 24:5843–5846; and Sinha, et al., (1984) *Nucl. Acids Res.*, 12:4539–4557, which are incorporated herein by reference.

b. Vectors

A number of vectors may be used to operably linked selected nucleic acids to heat shock promoters and mediate their replication, cloning and/or expression. "Cloning vectors" are useful for replicating and amplifying the foreign nucleic acids and obtaining clones of specific foreign nucleic acid-containing vectors. "Expression vectors" mediate the expression of the foreign nucleic acid. Some vectors are both cloning and expression vectors.

In general, the particular vector used to transport a foreign gene into the cell is not particularly critical. Any of the conventional vectors used for expression in the chosen host cell may be used.

An expression vector typically comprises a eukaryotic transcription unit or "expression cassette" that contains all the elements required for the expression of exogenous genes in eukaryotic cells. A typical expression cassette contains a promoter operably linked to the DNA sequence encoding a desired protein and signals required for efficient polyadenylation of the transcript.

Eukaryotic promoters typically contain two types of recognition sequences, the TATA box and upstream promoter elements. The TATA box, located 25–30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus, the long term repeat from various retroviruses such as murine leukemia virus, murine or Rous sarcoma virus and HIV. See, *Enhancers and*

*Eukaryotic Expression*, Cold Spring Harbor Press, Cold Spring Harbor, N.Y. 1983, which is incorporated herein by reference.

In addition to a promoter sequence, the expression cassette should also contain a transcription termination region downstream of the structural gene to provide for efficient termination. The termination region may be obtained from the same source as the promoter sequence or may be obtained from a different source.

If the mRNA encoded by the selected structural gene is to be efficiently translated, polyadenylation sequences are also commonly added to the vector construct. Two distinct sequence elements are required for accurate and efficient polyadenylation: GU or U rich sequences located downstream from the polyadenylation site and a highly conserved sequence of six nucleotides, AAUAAA, located 11–30 nucleotides upstream. Termination and polyadenylation signals that are suitable for the present invention include those derived from SV40, or a partial genomic copy of a gene already resident on the expression-vector.

In addition to the elements already described, the expression vector of the present invention may typically contain other specialized elements intended to increase the level of expression of cloned nucleic acids or to facilitate the identification of cells that carry the transduced DNA. For instance, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The expression vectors of the present invention will typically contain both prokaryotic sequences that facilitate the cloning of the vector in bacteria as well as one or more eukaryotic transcription units that are expressed only in eukaryotic cells, such as mammalian cells. The prokaryotic sequences are preferably chosen such that they do not interfere with the replication of the DNA in eukaryotic cells.

Selected genes are normally be expressed when the DNA sequence is functionally inserted into a vector. "Functionally inserted" means that it is inserted in proper reading frame and orientation and operably linked to proper regulatory elements. Typically, a gene will be inserted downstream from a promoter and will be followed by a stop codon, although production as a hybrid protein followed by cleavage may be used, if desired.

The vector normally contains, in addition to the gene of interest, one or more additional genes that encode selectable markers. The selectable markers can be for positive selection (e.g., the cells that express the marker gene survive whereas cells that do not express the selected gene die; such genes can encode, e.g., an antibiotic resistance) or for negative selection (e.g., the cells that express the marker gene die whereas cells that do not express the selected gene survive; such genes can encode, e.g., cytosine deaminase).

While a variety of vectors may be used, it should be noted that viral vectors such as retroviral vectors are useful for modifying eukaryotic cells because of the high efficiency with which the retroviral vectors transfect target cells and integrate into the target cell genome. Additionally, the retroviruses harboring the retroviral vector are capable of infecting cells from a wide variety of tissues.

Retroviral vectors are produced by genetically manipulating retroviruses. Retroviruses are called RNA viruses because the viral genome is RNA. Upon infection, this genomic RNA is reverse transcribed into a DNA copy which is integrated into the chromosomal DNA of transduced cells with a high degree of stability and efficiency. The integrated DNA copy is referred to as a provirus and is inherited by daughter cells as is any other gene. The wild type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site). See Mulligan, R. C., (1983) In: *Experimental Manipulation of Gene Expression*, M. Inouye (ed), 155–173; Mann, R., et al., (1983) *Cell*, 33:153–159; Cone, R. D. and R. C. Mulligan, (1984) *Proceedings of the National Academy of Sciences, U.S.A.*, 81:6349–6353.

Retroviral vectors are particularly useful for modifying cells because of the high efficiency with which the retroviral vectors transduce target cells and integrate into the target cell genome. See Miller, A. D., (1992) supra. Retroviruses harboring the retroviral vector are capable of infecting dividing cells from a wide variety of tissues. These vectors have the ability to stably integrate the transferred gene sequences into the chromosomal DNA of target cells.

The design of retroviral vectors is well known to one of skill in the art. See Singer, M. and Berg, P. supra. In brief, if the sequences necessary for encapsidation (or packaging of retroviral RNA into infectious virions) are missing from the viral genome, the result is a cis acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including European Patent Application EPA 0 178 220, U.S. Pat. No. 4,405,712, Gilboa, (1986) *Biotechniques* 4:504–512; Mann, et al., (1983) *Cell* 33:153–159; Cone and Mulligan, (1984) *Proc. Natl. Acad. Sci. USA* 81:6349–6353; Eglitis, M. A, et al. (1988) *Biotechniques* 6:608–614; Miller, A. D. et al. (1989) *Biotechniques* 7:981–990, Miller, A. D. (1992) Nature, supra, Mulligan, R. C. (1993), supra. and Gould, B. et al., and International Patent Application No. WO 92/07943 entitled "Retroviral Vectors Useful in Gene Therapy". The teachings of these patents and publications are incorporated herein by reference.

In addition to the retroviral vectors mentioned above, cells may be transformed with adenoviruses or adenoassociated viral vectors. See, e.g., *Methods in Enzymology*, Vol. 185, Academic Press, Inc., San Diego, Calif. (D. V. Goeddel, ed.) (1990) or M. Krieger (1990), *Gene Transfer and Expression—A Laboratory Manual*, Stockton Press, New York, N.Y., and the references cited therein. Adenoviruses are double stranded, linear DNA viruses that cause the "common cold", pneumonia, conjunctivitis and other illnesses. There are 42 serotypes of adenovirus known to infect humans.

Adenoviruses typically enter cells by receptor-mediated endocytosis. The specific receptor is unknown. Following internalization, the genome of the vector likely does not integrate into the host genome but instead functions episomally. This leads to only transient gene expression and also avoids random genome integration and its potential problems such as induced tumorigenicity.

Adeno-associated viruses (AAVs) require helper viruses such as adenovirus or herpes virus to achieve productive infection. In the absence of helper virus functions, AAV integrates (site-specifically) into a host cell's genome, but the integrated AAV genome has no pathogenic effect. The integration step allows the AAV genome to remain genetically intact until the host is exposed to the appropriate environmental conditions (e.g., a lytic helper virus), whereupon it re-enters the lytic life-cycle. Samulski (1993), *Current opinion in Genetic and Development,* 3:74–80, and the references cited therein provides an overview of the AAV life cycle. See also West et al. (1987), *Virology,* 160:38–47; Carter et al. (1989), U.S. Pat. No. 4,797,368; Carter et al. (1993), WO 93/24641; Kotin (1994), *Human Gene Therapy,* 5:793–801; Muzyczka (1994), *J. Clin. Invest.,* 94:1351 and Samulski, supra, for an overview of AAV vectors.

Recombinant AAV vectors (rAAV vectors) deliver foreign nucleic acids to a wide range of mammalian cells (Hermonat & Muzycka (1984) *Proc Natl Acad Sci USA* 81:6466–6470; Tratschin et al. (1985) *Mol Cell Biol* 5:3251–3260), integrate into the host chromosome (Mclaughlin et al. (1988) *J Virol* 62: 1963–1973), and show stable expression of the transgene in cell and animal models (Flotte et al. (1993) *Proc Natl Acad Sci USA* 90:10613–10617). Moreover, unlike retroviral vectors, rAAV vectors are able to infect non-dividing cells (Podsakoff et al. (1994) *J Virol* 68:5656–66; Flotte et al. (1994) *Am. J. Respir. Cell Mol. Biol.* 11:517–521). Further advantages of rAAV vectors include the lack of an intrinsic strong promoter, thus avoiding possible activation of downstream cellular sequences, and their naked icosahedral capsid structure, which renders them stable and easy to concentrate by common laboratory techniques.

rAAV vectors have several properties which make them preferred gene delivery systems in clinical settings. They have no known mode of pathogenesis and 80 % of people in the United States are currently seropositive for AAV (Blacklow et al. (1971) *J Natl Cancer Inst* 40:319–327; Blacklow et al. (1971) *Am J Epidemiol* 94:359–366). Because rAAV vectors have little or no endogenous promoter activity, specific promoters may be used, depending on target cell type. rAAV vectors can be purified and concentrated so that multiplicities of infection exceeding 1.0 can be used in transduction experiments. This allows virtually 100% of the target cells in a culture to be transduced, eliminating the need for selection of transduced cells.

Plasmids designed for producing recombinant vaccinia, such as pGS62, (Langford, C. L. et al. (1986), *Mol. Cell. Biol.,* 6:3191–3199) may also be used. Finally, nonpathogenic vectors derived from HIV have been reported to transform non-dividing cells, and may also be used.

Whatever the vector is used, generally the vector is genetically engineered to contain, in expressible form, a gene of interest. The particular gene selected will depend on the intended treatment. Examples of such genes of interest are described below at Section e below.

The vectors further usually comprise selectable markers which result in nucleic acid amplification such as the sodium, potassium ATPase, thymidine kinase, aminoglycoside phosphotransferase, hygromycin B phosphotransferase, xanthine-guanine phosphoribosyl transferase, CAD (carbamyl phosphate synthetase, aspartate transcarbamylase, and dihydroorotase), adenosine deaminase, dihydrofolate reductase, and asparagine synthetase and ouabain selection. Alternatively, high yield expression systems not involving nucleic acid amplification are also suitable, such as using a baculovirus vector in insect cells.

When nucleic acids other than plasmids are used the nucleic acids can contain nucleic acid analogs, for example, the antisense derivatives described in a review by Stein, et al., (1993) *Science* 261:1004–1011, and in U.S. Pat. Nos. 5,264,423 and 5,276,019, the disclosures of which are incorporated herein by reference.

c. In Vitro Gene Transfer

There are several well-known methods of introducing nucleic acids into animal cells, any of which may be used in the present invention. These include: calcium phosphate precipitation, fusion of the recipient cells with bacterial protoplasts containing the DNA, treatment of the recipient cells with liposomes containing the DNA, DEAE-dextran, receptor-mediated endocytosis, electroporation, micro-injection of the DNA directly into the cells, infection with viral vectors, etc.

For in vitro applications, the delivery of nucleic acids can be to any cell grown in culture, whether of plant or animal origin, vertebrate or invertebrate, and of any tissue or type. In preferred embodiments, the cells will be animal cells, more preferably mammalian cells, and most preferably human cells.

Contact between the cells and the genetically engineered nucleic acid constructs, when carried out in vitro, takes place in a biologically compatible medium. The concentration of nucleic acid varies widely depending on the particular application, but is generally between about 1 µmol and about 10 mmol. Treatment of the cells with the nucleic acid is generally carried out at physiological temperatures (about 37° C.) for periods of time of from about 1 to 48 hours, preferably of from about 2 to 4 hours.

In one group of preferred embodiments, a nucleic acid is added to 60–80% confluent plated cells having a cell density of from about $10^3$ to about $10^5$ cells/mL, more preferably about $2 \times 10^4$ cells/mL. The concentration of the suspension added to the cells is preferably of from about 0.01 to 0.2 µg/mL, more preferably about 0.1 µg/mL.

d. In Vivo Gene Transfer

Alternatively, the compositions of the present invention can also be used for the in vivo gene transfer, using methods which are known to those of skill in the art.

The insertion of genes into cells for the purpose of medicinal therapy is a rapidly growing field in medicine which has enormous clinical potential. Research in gene therapy has been on-going for several years, and has entered human clinical trials. Zhu, et al., (1993) *Science* 261: 209–211, incorporated herein by reference, describes the intravenous delivery of cytomegalovirus (CMV)-chloramphenicol acetyltransferase (CAT) expression plasmid using DOTMA-DOPE complexes. Hyde, et al., (1993) *Nature* 362:250–256, incorporated herein by reference, describes the delivery of the cystic fibrosis transmembrane conductance regulator (CFTR) gene to epithelia of the airway and to alveoli in the lung of mice, using liposomes. Brigham, et al., (1989) *Am. J. Med. Sci.* 298:278–281, incorporated herein by reference, describes the in vivo transfection of lungs of mice with a functioning prokaryotic gene encoding the intracellular enzyme chloramphenicol acetyltransferase (CAT).

For in vivo administration, the pharmaceutical compositions are preferably administered parenterally, i.e., intraarticularly, intravenously, intraperitoneally, subcutaneously, or intramuscularly. More preferably, the pharmaceutical compositions are administered intravenously or intraperitoneally by a bolus injection. For example, see Stadler, et al., U.S.

Pat. No. 5,286,634, which is incorporated herein by reference. Intracellular nucleic acid delivery has also been discussed in Straubringer, et al., (1983) METHODS IN ENZYMOLOGY, Academic Press, New York. 101:512–527; Mannino, et al., (1988) *Biotechniques* 6:682–690; Nicolau, et al., (1989) *Crit. Rev. Ther. Drug Carrier Syst.* 6:239–271, and Behr, (1993) *Acc. Chem. Res.* 26:274–278. Still other methods of administering therapeutics are described in, for example, Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578.

In certain embodiments, the pharmaceutical preparations may be contacted with the target tissue by direct application of the preparation to the tissue. The application may be made by topical, "open" or "closed" procedures. By "topical", it is meant the direct application of the pharmaceutical preparation to a tissue exposed to the environment, such as the skin, oropharynx, external auditory canal, and the like. "Open" procedures are those procedures which include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

The nucleic acid can also be administered in an aerosol inhaled into the lungs (see, Brigham, et al., (1989) *Am. J. Sci.* 298(4):278–281 or by direct injection at the site of disease (Culver, (1994) HUMAN GENE THERAPY, MaryAnn Liebert, Inc., Publishers, New York. pp. 70–71).

The methods of the present invention may be practiced in a variety of hosts. Preferred hosts include mammalian species, such as humans, non-human primates, dogs, cats, cattle, horses, sheep, and the like.

The amount of nucleic acid administered will depend upon the particular nucleic acid used, the disease state being diagnosed; the age, weight, and condition of the patient and the judgement of the clinician; but will generally be between about 0.01 and about 50 mg per kilogram of body weight; preferably between about 0.1 and about 5 mg/kg of body weight or about $10^8$–$10^{10}$ particles per injection.

For in vivo gene transfer, pharmaceutical compositions comprising selected vectors containing selected nucleic acids are preferably administered parenterally, i.e., intraarticularly, intravenously, intraperitoneally, subcutaneously, or intramuscularly. More preferably, the pharmaceutical compositions are administered intravenously or intraperitoneally by a bolus injection. For example, see Stadler, et al., U.S. Pat. No. 5,286,634, which is incorporated herein by reference. Intracellular nucleic acid delivery has also been discussed in Straubringer, et al., (1983) METHODS IN ENZYMOLOGY, Academic Press, New York. 101:512–527; Mannino, et al., (1988) *Biotechniques* 6:682–690; Nicolau, et al., (1989) *Crit. Rev. Ther. Drug Carrier Syst.* 6:239–271, and Behr, (1993) *Acc. Chem. Res.* 26:274–278. Still other methods of administering therapeutics are described in, for example, Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578.

Formulations suitable for administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged nucleic acid can be presented in unit-dose or multi-dose sealed containers, such as ampules and vials. Injection solutions and suspensions can be prepared from sterile powders, granules, and tablets of the kind previously described.

A vector dose which is sufficient to effect a beneficial therapeutic response in the patient over time, or to inhibit infection by a pathogen, is administered to a patient. A therapeutically effective dose is an amount sufficient to cure, or at least partially arrest, the symptoms of the disease and its complications. Effective doses of the compositions of the present invention, for the treatment of the above described conditions will vary depending upon many different factors, including means of administration, target site, physiological state of the patient, and other medicants administered. Thus, treatment dosages will need to be titrated to optimize safety and efficacy. In determining the effective amount of the vector to be administered, the physician evaluates the particular nucleic acid used, the disease state being diagnosed; the age, weight, and condition of the patient, circulating plasma levels, vector toxicities, progression of the disease, and the production of anti-vector antibodies. The size of the dose also will be determined by the existence, nature, and extent of any adverse side-effects that accompany the administration of a particular vector. Doses ranging from about 10 ng to 1 g, 100 ng to 100 mg, 1 μg to 10 mg, or 30–300 μg DNA per patient are typical. Doses generally range between about 0.01 and about 50 mg per kilogram of body weight; preferably between about 0.1 and about 5 mg/kg of body weight or about $10^8$–$10^{10}$ particles per injection. In general, the dose equivalent of a naked nucleic acid from a vector is from about 1 μg to 100 μg for a typical 70 kilogram patient, and doses of vectors which include a retroviral particle are calculated to yield an equivalent amount of inhibitor nucleic acid.

Prior to infusion, blood samples are obtained and saved for analysis. Between $10^8$ and $1\times10^{12}$ vectors are infused intravenously over 60–200 minutes. Vital signs and oxygen saturation by pulse oximetry are closely monitored. Blood samples are obtained 5 minutes and 1 hour following infusion and saved for subsequent analysis. At the physician's discretion, reinfusion is repeated every 2 to 3 months for a total of 4 to 6 treatments in a one year period.

After the first treatment, infusions can be performed on a outpatient basis at the discretion of the clinician. If the reinfusion is given as an outpatient, the participant is monitored for at least 4, and preferably 8 hours following the therapy.

If a patient undergoing infusion of a vector or transduced cell develops fevers, chills, or muscle aches, he/she receives the appropriate dose of aspirin, ibuprofen or acetaminophen. Patients who experience reactions to the infusion such as fever, muscle aches, and chills are premedicated 30 minutes prior to the future infusions with either aspirin, acetaminophen, or diphenhydramine. Meperidine is used for more severe chills and muscle aches that do not quickly respond to antipyretics and antihistamines. Vector infusion is slowed or discontinued depending upon the severity of the reaction.

e. Expression of a Functional Copy of a Gene

Some methods of gene therapy serve to compensate for a defect in an endogenous gene by integrating a functional copy of the gene into the host chromosome. The inserted gene replicates with the host DNA and is expressed at a level to compensate for the defective gene. Diseases amenable to treatment by this approach are often characterized by recessive mutations. That is, both copies of an endogenous gene must be defective for symptoms to appear. Such diseases include, for example, cystic fibrosis, sickle cell anemia, β-thalassemia, phenylketonuria, galactosemia, Wilson's disease, hemochromatosis, severe combined immunodeficiency disease, alpha-1-antitrypsin deficiency, albinism, alkaptonuria, lysosomal storage diseases, Ehlers-Danlos syndrome, hemophilia, glucose-6-phosphate dehydrogenase deficiency, agammaglobulimenia, diabetes insipidus, Lesch-Nyhan syndrome, muscular dystrophy, Wiskott-Aldrich syndrome, Fabry's disease, fragile X-syndrome, and the like. Other recessive mutations are known in the art, and the use of the methods of the present invention to treat them is contemplated herein.

There are several methods for introducing an exogenous functional gene to compensate for the above genetic defects. In one approach, cells are removed from a patient suffering from the disease and contacted with a vector in vitro. Cells should be removed from a tissue type in which disease symptoms are manifested. If the cells are capable of replication, and the vector used includes a selective marker, cells having internalized and expressed the marker can be selected. Particularly if selection is not performed, it is important that the frequency of gene transfer into cells be high, for example, at least about 1, 5, 10, 25 or 50% of cells.

After integration of the vector into the cellular genome, and optionally, selection, cells are reintroduced into the patient. In this application, and others discussed below (except site-specific recombination to correct dominant mutations), it is not necessary that the gene supplied be delivered to the same site as is occupied by the defective gene for which it is compensating.

Alternatively, the nucleic acid can be introduced directly into a patient as a pharmaceutical composition. The complex is delivered to the tissue(s) affected by the genetic disorder being treated in a therapeutically effective dose.

In this and other methods, a therapeutically effective dose is an amount sufficient to cure, or at least partially arrest, the symptoms of the disease and its complications. Effective doses of the compositions of the present invention, for the treatment of the above described conditions will vary depending upon many different factors, including means of administration, target site, physiological state of the patient, and other medicants administered. Thus, treatment dosages will need to be titrated to optimize safety and efficacy. Doses ranging from about 10 ng to 1 g, 100 ng to 100 mg, 1 μg to 10 mg, or 30–300 μg DNA per patient are typical. Routes of administration include oral, nasal, gastric, intravenous, intradermal and intramuscular.

i. Stem Cell Therapy

The nucleic acids can also be used to transfect embryonic stem cells or zygotes to achieve germline alterations. See Jaenisch, (1988) *Science,* 240:468–1474; Gordon et al. (1984) *Methods Enzymol.* 101:414; Hogan et al., (1986) *Manipulation of the Mouse Embryo: A Laboratory Manual,* C.S.H.L. N.Y.; and Hammer et al. (1985) *Nature* 315:680; Gandolfi et al. (1987) *J. Reprod. Fert.* 81:23–28; Rexroad et al. (1988) *J. Anim. Sci.* 66:947–953 and Eyestone et al. (1989) *J. Reprod. Fert.* 85:715–720; Camous et al. (1984) *J. Reprod. Fert.* 72:779–785; Heyman et al. (1987) *Theriogenology* 27:5968. However, these methods are presently more suitable for veterinary applications that human treatment due to ethical and regulatory constraints in manipulating human embryos.

As an example, cystic fibrosis (CF) is a usually fatal recessive genetic disease, having a high incidence in Caucasian populations. The gene responsible for this disease was isolated by Riordan et al, (1989) *Science* 245:1059–1065. It encodes a protein called the cystic fibrosis transmembrane conductance regulator (CFTR) which is involved in the transfer of chloride ions ($Cl^-$) through epithelial cell membranes. Mutations in the gene cause defects of $Cl^-$ secretion in epithelial cells leading to the various clinical manifestations. Although CF has a number of symptoms including thickened exocrine gland secretions, pancreatic deficiency, intestinal blockage and malabsorption of fat, the most serious factor affecting mortality is chronic lung disease. Accordingly, to treat a CF patient, a vector containing a coding sequence for a functional CFTR gene product can be introduced into the patient via nasal administration so that the nucleic acid composition reaches the lungs. The dose of vector is preferably about $10^8$–$10^{10}$ particles.

As another example, defects in the α or γ globin genes (see McDonagh & Nienhuis in *Hematology of Infancy and Childhood* (eds. Nathan & Oski, Saunders, Pa., 1992) at pp. 783–879) can be compensated for by ex vivo treatment of hemopoietic stem cells with a nucleic acid containing a functional copy of the gene. The gene integrates into the stem cells which are then reintroduced into the patient. Defects in the gene responsible for Fanconi Anemia Complement Group C can be treated by an analogous strategy (see Walsh et al., (1994) *J. Clin. Invest.* 94:1440–1448).

ii. Cancer Therapy

Other applications include the introduction of a functional copy of a tumor suppressor gene into cancerous cell or cells at risk of becoming cancerous. D. Pardoll, (1992) "Immunotherapy with cytokine gene-transduced tumor cells: the next wave in gene therapy for cancer", *Curr. Opin. Oncol.* 4:1124–1129; Uckert and Walther, (1994) "Retrovirus-mediated gene transfer in cancer therapy", *Pharmac. Ther.* 63:323–347; Individuals having defects in one or both copies of an endogenous tumor suppressor gene are particularly at risk of developing cancers. For example, Li-Fraumeni syndrome is a hereditary condition in which individuals receive mutant p53 alleles, resulting in the early onset of various cancers (Harris, (1993) *Science* 262:1980–1981, Frebourg et al., (1992) *PNAS* 89:6413–6417; Malkin et al., (1990) *Science* 250:1233). Expression of a tumor suppressor gene in a cancerous dell or a cell at risk of becoming cancerous is effective to prevent, arrest and/or reverse cellular proliferation and other manifestations of the cancerous state. Suitable tumor suppressor genes for use in the invention include p53 (Buchman et al., (1988) *Gene* 70:245–252), APC, DCC, Rb, WT1, and NF1 (Marx, (1993) *Science* 260:751–752; Marshall, (1991) *Cell* 64:313–326). Nucleic acid constructs bearing a functional copy of a tumor suppressor gene are usually administered in vivo by the route most proximal to the intended site of action. For example, skin cancers can be treated by topical administration and leukemia by intravenous administration. The methods of the invention are useful for treating a wide variety of cancers, among them prostate, glyoma, ovarian, and mammary tumors.

iii. Angiogenesis Therapy

Local disruptions in blood flow, e.g. coronary artery disease, peripheral arterial occlusive disease, and cerebral vascular disease (stroke) are among the most common causes of morbidity and mortality. These disorders are all caused by insufficient tissue perfusion.

The discovery of polypeptides capable of stimulating angiogenesis has led to several investigations towards the ability to improve local perfusion based on such angiogenic factors, e.g. vascular endothelial growth factor (VEGF), fibroblast growth factor (FGF), platelet derived growth factor (PDGF). L. -Q. Pu et al. (1993) *Circulation,* 88:1–147; Symes and Sniderman, (1994) *Curr. Opin. Lipidol.* 5:305–312; see also U.S. Pat. Nos. 5,219,759, 5,512,545, 5,491,220, 5,464,943, 5,464,774, 5,360,896, 5,175,383, 5,155,214. For example, it has been reported that revascularization occurs after intravenous administration of ECGF for 10 days. Injection in a remote site does not lead to increased vascularization. A dose dependency was clearly established. Angiogenic factors are toxic when used in high concentration, so local application appears necessary. VEGF appears a better choice since it can be secreted and it has mitotic activity.

M. Hoeckel et al. (1993) *Arch. Surg.* 128:423–429, has listed the following criteria for therapeutic use of an angiogenic factor:

1) Able to stimulate neovascularization
2) Negligible local and systemic side effects
3) High efficiency in nanomolar and picomolar range
4) Demonstrated dose-response relation
5) Chemically defined and easy to handle
6) Can be produced on a large scale Localized heat induction of genetically engineered cells provides the localized expression of angiogenic factors, and minimizes systemic effects.

f. Suppression of Gene Expression

Methods of gene therapy using the nucleic acid constructs of the invention can also be used for prophylactic or therapeutic treatment of patients or cells, infected with or at risk of being infected with, a pathogenic microorganism, such as HIV. The effectiveness of antisense molecules in blocking target gene functions has been demonstrated in a number of different systems (Friedman et al. (1988), *Nature* 335:452–54, Malim et al., (1989) *Cell* 58:205–14 and Trono et al., (1989) *Cell* 59:113–20). The vector used includes a DNA segment encoding an antisense transcript, which is complementary to a segment of the gene. Where the gene is from a pathogenic microorganism, it should preferably play an essential role in the life cycle of the and should also be unique to the microorganism (or at least absent from the genome of the patient undergoing therapy). For example, suitable sites for inhibition on the HIV virus includes TAR, REV or nef (Chatterjee et al., (1992) *Science* 258:1485–1488). Rev is a regulatory RNA binding protein that facilitates the export of unspliced HIV pre mRNA from the nucleus. Malim et al., (1989) *Nature* 338:254. Tat is thought to be a transcriptional activator that functions by binding a recognition sequence in 5' flanking mRNA. Karn & Graeble, (1992) *Trends Genet.* 8:365. The nucleic acid is introduced into leukocytes or hemopoietic stem cells, either ex vivo or by intravenous injection in a therapeutically effective dose. The treatment can be administered prophylactically to HIV⁻ persons, or to persons already infected with HIV.

g. Cells to be Transformed

The compositions and methods of the present invention are used to transfer genes into a wide variety of cell types, in vivo and in vitro. Among those most often targeted for gene therapy are precursor (stem) cells, especially hematopoietic stem cells. Other cells include those of which a proportion of the targeted cells are nondividing or slow dividing. These include, for example, fibroblasts, keratinocytes, endothelial cells, skeletal and smooth muscle cells, osteoblasts, neurons, quiescent lymphocytes, terminally differentiated cells, slow or non-cycling primary cells, parenchymal cells, lymphoid cells, epithelial cells, bone cells, etc. The methods and compositions can be employed with cells of a wide variety of vertebrates, including mammals, and especially those of veterinary importance, e.g, canine, feline, equine, bovine, ovine, caprine, rodent, lagomorph, swine, etc., in addition to human cell populations.

To the extent that tissue culture of cells may be required, it is well known in the art. Freshney (1994) (*Culture of Animal Cells, a Manual of Basic Technique*, third edition Wiley-Liss, New York); Kuchler et al. (1977) *Biochemical Methods in Cell Culture and Virology*, Kuchler, R. J., Dowden, Hutchinson and Ross, Inc., and the references cited therein provides a general guide to the culture of cells. Cultured cell systems often will be in the form of monolayers of cells, although cell suspensions are also used.

Gene therapy relies on the efficient delivery of therapeutic genes to target cells. Most of the somatic cells that have been targeted for gene therapy, e.g., hematopoietic cells, skin fibroblasts and keratinocytes, hepatocytes, endothelial cells, muscle cells and lymphocytes, are normally non-dividing. Retroviral vectors, which are the most widely used vectors for gene therapy, unfortunately require cell division for effective transduction (Miller et al., (1990) *Mol. Cell. Biol.* 10:4239–4242). This is also true with other gene therapy vectors such as the adeno-associated vectors (Russell et al., (1991) *Proc. Natl. Acad. Sci. USA* 91:8915–8919; Alexander et al., (1994) *J. Virol.* 68:8282–8287; Srivastava, (1994) *Blood Cells* 20:531–538). Recently, HIV-based vectors has been reported to transfect non-dividing cells. Nonetheless, the majority of stem cells, a preferred target for many gene therapy treatments, are normally not proliferating. Thus, the efficiency of transduction is often relatively low, and the gene product may not be expressed in therapeutically or prophylactically effective amounts. This has led investigators to develop techniques such as stimulating the stem cells to proliferate prior to or during gene transfer (e.g., by treatment with growth factors) Pretreatment with 5-fluorouracil, infection in the presence of cytokines, and extending the vector infection period to increase the likelihood that stem cells are dividing during infection, but these have met with limited success.

h. Detection of Foreign Nucleic Acids

After a given cell is transduced with a nucleic acid construct that encodes a gene of interest under the control of a hsp promoter, it is important to detect which cells or cell lines express the gene product and to assess the level of expression of the gene product in engineered cells. This requires the detection of nucleic acids that encode the gene products.

Nucleic acids and proteins are detected and quantified herein by any of a number of means well known to those of skill in the art. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like. The detection of nucleic acids proceeds by well known methods such as Southern analysis, northern analysis, gel electrophoresis, PCR, radiolabeling, scintillation counting, and affinity chromatography.

The selection of a nucleic acid hybridization format is not critical. A variety of nucleic acid hybridization formats are known to those skilled in the art. For example, common formats include sandwich assays and competition or displacement assays. Hybridization techniques are generally described in NUCLEIC ACID HYBRIDIZATION, A PRACTICAL APPROACH, Ed. Hames, B. D. and Higgins, S. J., IRL Press, 1985.

The sensitivity of the hybridization assays may be enhanced through use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al. (1987), U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990), C&EN 36–47; *The Journal Of NIH Research* (1991), 3: 81–94; (Kwoh et al. (1989), *Proc. Natl. Acad. Sci. USA*, 86:1173; Guatelli et al. (1990), *Proc. Natl. Acad. Sci. USA*, 87:1874; Lomell et al. (1989), *J. Clin. Chem.*, 35:1826; Landegren et al. (1988), *Science*, 241:1077–1080; Van Brunt (1990), *Biotechnology*, 8:291–294; Wu and Wallace (1989), *Gene*, 4:560; Barringer et al. (1990), *Gene*, 89:117, and Sooknanan and Malek (1995), *Biotechnology*, 13:563–564. Improved methods of cloning in vitro amplified nucleic acids are described in Wallace et al., U.S. Pat. No. 5,426,039. Other methods recently described in the art are the nucleic acid sequence based amplification (NASBA™, Cangene, Mississauga, Ontario) and Q Beta Replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation.

Oligonucleotides for use as probes, e.g., in in vitro amplification methods, for use as gene probes, or as inhibitor components are typically synthesized chemically according to the solid phase phosphoramidite triester method described by Beaucage and Caruthers (1981), *Tetrahedron Letts.*, 22(20):1859–1862, e.g., using an automated synthesizer, as described in Needham-Van Devanter et al. (1984), *Nucleic Acids Res.*, 12:6159–6168. Purification of oligonucleotides, where necessary, is typically performed by either native acrylamide gel electrophoresis or by anion-exchange HPLC as described in Pearson and Regnier (1983), *J. Chrom.*, 255:137–149. The sequence of the synthetic oligonucleotides can be verified using the chemical degradation method of Maxam and Gilbert (1980) in Grossman and Moldave (eds.) Academic Press, New York, *Methods in Enzymology*, 65:499–560.

An alternative means for determining the level of expression of the gene is in situ hybridization. In situ hybridization assays are well known and are generally described in Angerer et al. (1987), *Methods Enzymol.*, 152:649–660. In an in situ hybridization assay cells are fixed to a solid support, typically a glass slide. If DNA is to be probed, the cells are denatured with heat or alkali. The cells are then contacted with a hybridization solution at a moderate temperature to permit annealing of specific probes that are labelled. The probes are preferably labelled with radioisotopes or fluorescent reporters.

i. Detection of Foreign Gene Products

The expression of the gene of interest under the control of a n hsp promoter to produce a product may be detected or quantified by a variety of methods. Preferred methods involve the use of specific antibodies.

Methods of producing polyclonal and monoclonal antibodies are known to those of skill in the art. See, e.g., Coligan (1991), CURRENT PROTOCOLS IN IMMUNOLOGY, Wiley/Greene, NY; and Harlow and Lane (1989), ANTIBODIES: A LABORATORY MANUAL, Cold Spring Harbor Press, NY; Stites et al. (eds.) BASIC AND CLINICAL IMMUNOLOGY (4th ed.) Lange Medical Publications, Los Altos, Calif., and references cited therein; Goding (1986), MONOCLONAL ANTIBODIES: PRINCIPLES AND PRACTICE (2d ed.) Academic Press, New York, N.Y.; and Kohler and Milstein (1975), Nature, 256:495–497. Such techniques include antibody preparation by selection of antibodies from libraries of recombinant antibodies in phage or similar vectors. See, Huse et al. (1989), *Science*, 246: 1275–1281; and Ward et al. (1989), *Nature*, 341:544–546. Specific monoclonal and polyclonal antibodies and antisera will usually bind with a $K_D$ of at least about 0.1 mM, more usually at least about 1 µM, preferably at least about 0.1 µM or better, and most preferably, 0.01 µM or better.

The presence of a desired polypeptide (including peptide, transcript, or enzymatic digestion product) in a sample may be detected and quantified using Western blot analysis. The technique generally comprises separating sample products by gel electrophoresis on the basis of molecular weight, transferring the separated proteins to a suitable solid support, (such as a nitrocellulose filter, a nylon filter, or derivatized nylon filter), and incubating the sample with labeling antibodies that specifically bind to the analyte protein. The labeling antibodies specifically bind to analyte on the solid support. These antibodies are directly labeled, or alternatively are subsequently detected using labeling agents such as antibodies (e.g., labeled sheep anti-mouse antibodies where the antibody to an analyte is a murine antibody) that specifically bind to the labeling antibody.

3. Heat Induction of the hsp Promoter

Central to the present invention is the ability to selectively activate heat-inducible promoters using localized heat. In particular, it is important to controllably heat cells within a target area located within deep tissue while minimizing heating of surrounding cells.

Localized heating of deep lying tissues can be accomplished by invasive or noninvasive methods (without opening the skin). Among the invasive methods, the introduction of a catheter with a heated tip can be used. Alternatively, a catheter with an optical guide can be used. A laser beam can then be directed through the catheter to the targeted tissue and heat can be deposited using direct radiation (for example using infrared light). Although irradiation by laser has been proposed for heating deep tissue, its use in medicine has been limited by optical absorption and thermal diffusion.

In the preferred embodiment, local heating is achieved by noninvasive means. FIG. 1, taken from Ernst et al., PRINCIPLES OF NUCLEAR RADIATION IN ONE AND TWO DIMENSIONS, Oxford University Press, 1987, illustrates the attenuation of electromagnetic and ultrasound radiation. For heating of deep lying tissues, a transition area in FIG. 1 is used (since both absorption and penetration are needed). The X-ray region of the spectrum uses ionizing radiation which is hazardous. The radiofrequency region has a wavelength of more than 10 cm. Acoustical radiation is strongly absorbed for wavelengths below 1 mm. Since the ability to focus is limited to approximately half the wavelength, a focus diameter of 5 cm or more can be attained by radiofrequency. This is generally not localized enough to treat small lesions. Ultrasound can be applied with a short enough wavelength to be localized and can penetrate deeply and is to some extent absorbed by body tissues. Therefore, the preferred method for noninvasive local heating is focused ultrasound.

It is known that ultrasound can be aimed at a defined target area, and that prolonged exposure of living tissues to ultrasound can raise the temperature of the exposed tissue. In particular focused ultrasound has been known to be very effective to locally heat tissue so long as there is an acoustic path from the surface to the lesion free of air and bone. Lele, L. L. (1962) "A simple method for production of trackless focal lesions with focused ultrasound: physical factors," *J. Physiol* 160:494–512; Fry et al., (1978) "Tumor irradiation with intense ultrasound", *Ultrasound Med. Biol.* 4:337–341. Using an array of ultrasound transducers with high precision of heat deposition, focused ultrasound can be delivered at high intensity to a defined very small area of deep tissue. Focus of the ultrasound is achieved by the shape of the transducer (spherical, parabolical) and/or by combining several different transducer elements and combining their ultrasound waves with individually adjusted phases in order to provide a focal spot. The principles of ultrasound can be found in, for example, Bushberg J. T. et al., THE ESSENTIAL PHYSICS OF MEDICAL IMAGING, Williams and Wilkins, Baltimore, 1994, pp. 367–526.

In general, published studies have either sought to use ultrasound to deliberately burn tissue, or to image tissues without significantly raising their temperature. See, e.g., McAllister et al. (1994) *Teratology* 51:191; Cline et al. (1992) "MR-guided focused ultrasound surgery" *J. Comp. Asst. Tomog.* 16:956–965. Angles et al. (1991) *Teratology* 42:285 reported that ultrasound can activate heat shock genes in the absence of any detectable rise in temperature. In U.S. Pat. No. 5,447,858, a soybean hsp promoter was recombined with a heterologous gene, introduced into plant cells, and the hsp promoter was activated using the "heat of day" (column 11, lines 15–25) or incubation at, for example, 42.5° C. (column 11, line 37). High intensity focused ultrasound has been used to ablate tumors in animal models (Lele (1962), *J. Physiol.* 160:494–512; Fry et al. (1978), *Ultrasound Med. Biol.* 4:337–341) and is a proposed surgical technique for treating liver tumors (ter Harr et al. (1991), *Phys. Med. Biol.* 36:1495–1501; ter Harr et al. (1991), *Min. Invas. Ther.* 1:13–19).

In contrast, the present invention sets out to deliberately heat tissue within a target volume, but in a finely controlled fashion within a defined range of temperatures. In the past, several factors have limited the use of ultrasound to locally heat tissue: 1) the inability to precisely pinpoint the exact location of heat deposition due to interference near air/water, water/bone, and fat/water boundaries, 2) the inability to precisely quantify temperature elevation, and 3) the inability to simultaneously visualize the target tissue and surrounding tissues to monitor extent and effects of ultrasound heating. One possibility is to use a combination of focused ultrasound and magnetic resonance imaging (MRI). Cline et al. (1994) *Magn. Reson. Med.* 31:628–636, Cline et al. (1995) *J. Comp. Asst. Tom.* 16:956–965, De Poorter (1995) *Magn. Reson. Med.* 33:74–81.

It should be noted that the heat shock promoter may be activated by phenomena other than ultrasound that can raise body temperature (e.g., fever, hot shower, stress). Thus, it is appropriate to stringently control these variables (closely monitor a patient's temperature, avoid hot showers, avoid stress-producing environments) during the duration of treatment. Another approach is to limit the duration of the gene therapy.

In addition, heat can activate endogenous heat shock genes under the control of endogenous hsp promoters. The interaction between the processes will be studied.

4. Imaging of Temperature

An element of the noninvasive use of focused ultrasound is that one needs to assure that 1) the heated area corresponds with the target tissue, and 2) the temperature elevation corresponds with the target temperature. The first problem requires anatomical visualization, and the second one visualization of temperature distribution.

Whereas ultrasound can in principle be used for both purposes, its precision is considered inadequate for this purpose.

Cline et al., (1992) *J. Comp. Asst. Tomog.* 16:956–963, described the combination of Magnetic Resonance Imaging (MRI) and focused ultrasound, in which MRI is used to visualize and map the target area and to visualize and map the temperature distribution. The principles of MRI can be found in for example Stark D. D. and Bradley, W. G., MAGNETIC RESONACE IMAGING, Mosby Year Book, 1992, pp. 1–521.

Imaging of temperature can be accomplished by MRI in three ways: 1) using the spin-lattice (Tl) relaxation dependence on temperature; 2) using the diffusion constant dependence of water on temperature; and 3) using the Larmor-precession frequency dependence of water protons on temperature. It is increasingly clear that the third method is the preferred method since it is rather independent of most intra- and extracellular processes, and it can be measured very rapidly in an imaging method. Cline et al. (1994), "MR temperature mapping of focused ultrasound surgery," *Magn. Reson. Med.* 31:628–636; De Poorter et al. (1995), "Noninvasive MRI thermometry with the proton resonance frequency (PRF) method: In vivo results in human muscle", *Magn. Reson. Med.* 33:74–819; Hall et al. (1985), "Mapping of pH and temperature distribution using chemicalshift-resolved tomography," *J. Magn. Reson.* 65:501–505 (J. de Zwart et al. (1996), *J. Magn. Reson.* Series B, 112:86–90 and references therein).

Proton resonance frequency (PRF) depends on temperature. PRF information is obtained from the phase shift in gradient echo images. MRI Thermometry based on PRF shows little if any dependence on intra- and extracellular composition. Imaging speed is essential for two reasons: avoiding motion artifacts, and limiting effects of thermal conduction on quantitation of temperature increase. In order to minimize total imaging time, the time between successive excitations (repetition time, "TR") should be short. However, echo time ("TE") should be long to allow phase accumulation. Using this technology, it is feasible to acquire 3D images within 5 seconds with a spatial resolution of about 3–4 mm, and a temperature accuracy of about 2 degrees C.

In the preferred embodiment, a MRI guided focused ultrasound is used as is described in Cline et al., (1995) *Magn. Reson. Imaging,* 194:731–737. In future embodiments, the single ultrasound transducer under mechanical control described by Cline et al. will preferably be replaced with an array of transducers under electronic control to steer the focus electronically as described by Fan, X. and Hynynen, (1995) *Med. Phys.* 22(3):297–306.

EXAMPLES

The following examples are offered solely for the purposes of illustration, and are intended neither to limit nor to define the invention.

Example 1

Example 1 describes the use of focused ultrasound (FUS) guided by MRI to heat a region of a transformed human tumor having preselected three-dimensional coordinates, wherein the heating activates a genetically engineered therapeutical gene which is under the control of an hsp70 heat shock promoter.

A. Materials and Methods

Figure 2:
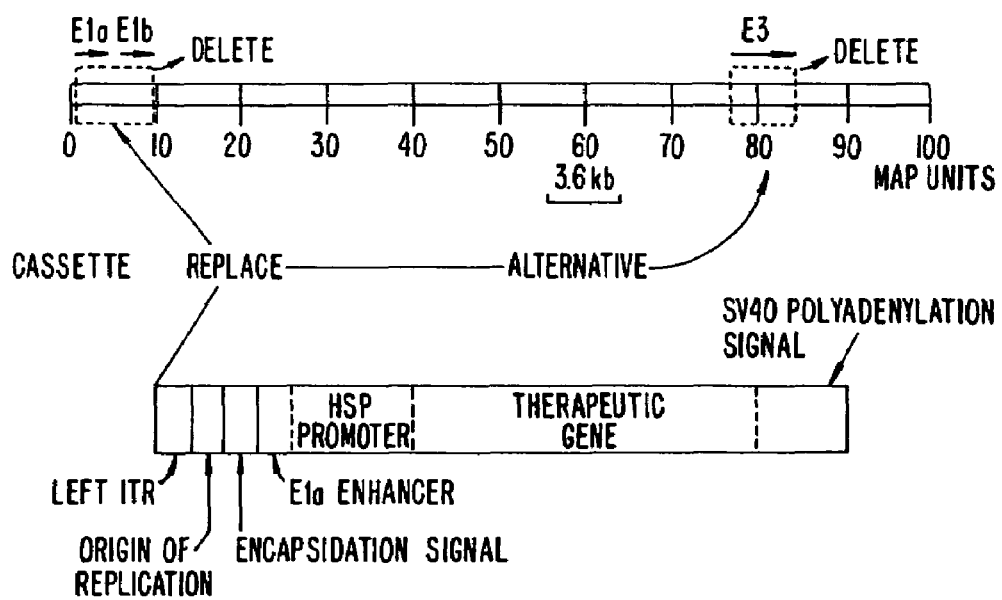
FIG. 2 depicts a prototypic adenovirus vector.

1. Preparation of a Vector Containing an hsp Promoter Operably Linked to a Therapeutic Gene Vectors derived from adenovirus serotype 5 are used in this example. S. L. Brody and R. G- Crystal (1994), "Adenovirus-Mediated In Vivo Gene Transfer," *Ann. N.Y. Acad. Sci.* 716:90–101. The E1A and E1b region are optionally deleted to prevent replication (see FIG. 2). The E3 region is also optionally be deleted to provide a 7.5 kb region for exogenous DNA.

The human hsp-70B promoter is used, as it is strictly heat regulated and can promote a several thousand fold increase in expression upon induction (M. Dreano et al. (1986), "High level heat-regulated synthesis of proteins in eukaryotic cells," *Gene* 49:1). The sequence of the human hsp-70B promoter is given in FIG. 3C, together with its analogs from *Drosophila* and changes in promoter activity using insertions. Voelmy (1994), *Crit. Rev. Euk. Gene Exp.* 4: 1357. HSEII and HSEI refer to the common heat shock elements II and I respectively. The insertions can alter promoter efficiency (R. Voellmy et al. (1994), "Transduction of the stress signal and mechanisms of transcriptional regulation of heat shock/stress protein gene expression in higher eukaryotes," *Crit. Rev. in Eukar. Gene Expr.* 4:357–401). It should be noted here that hsp-70B is not activated by adenovirus gene products (M. C. Simon et al. (1987), "Selective induction of human heat shock gene transcription by the adenovirus E1A products, including the 13S E1A product," *Mol. Cell Biol.* 7:2884.

The vector is constructed by inserting into a vector a cassette containing the human interleukin-2, as described in Addison et al. (1995) *Proc. Nat. Acad. Sci. U.S.A.* 92: 8522–6 (other lymphokines such as IL-1, IL-4, tumor necrosis factor, etc. may be used; see, e.g., U.S. Pat. No. 4,992, 367, and Furutani et al. (1986), *Nuc. Acids Res.* 14:3167–79) except that the gene will be under the control of the human hsp70 promoter in place of the E1 or E3 position of the adenovirus type 5 genome. The *E. coli* LacZ gene is optionally included in the vector as a reporter gene. Its product, β-galactosidase, can be easily detected and quantified by its specific substrate. An SV40 polyadenylation is optionally used together with a inverse terminal repeat (ITR) as an encapsidation signal and enhancer (see FIG. 1). Construction of the vector is accomplished using a plasmid containing the cassette and the adenovirus type 5 sequences used for homologous recombination with the E1- or E3-adenovirus genomic DNA.

The modified adenovirus is grown in 293 cells, a transformed human embryonic kidney call line that expresses E1 proteins, providing (in case of a replication-deficient adenovirus) E1 functions to allow for the production of virus. Viral vectors are produced in titers of up to $10^{12}$ plaque forming units per mL.

2. Administration of the Vector to a Patient

The vector is administered systemically to a patient that has been diagnosed as having a mammary adenocarcinoma. Preferably, 1 µg to 100 µg vector DNA are injected in 0.1–2 mls of a saline solution directly into the tumor. Alternatively, approximately 10 µg to 1 mg vector DNA are intravenously injected in 1–5 mls of a saline solution.

The presence and/or of the vector is determined by obtaining a biopsy of the cancerous tissue and demonstrating the presence of the gene or gene product by well known Northern, Southern or Western blotting techniques, or by detecting the activity of the optional reporter LacZ gene.

3. Focused Ultrasound Heating

A patient is placed on a special bed (e.g., General Electric Co., Milwaukee, Wis., as described in Cline et al. 1994 and 1995, supra) and moved into the magnet of a magnetic resonance imaging (MRI) instrument (e.g., 1.5T MR Imaging system by Signa, GE Medical Systems, Milwaukee, Wis.). The MRI instrument is equipped with a focused ultrasound (FUS) device (Specialty Engineering Associates, Milpitas, Calif.) under computer control. Specifically, the FUS device can be incorporated in the bed of the MRI in such a way that the transducer can be freely moved under the patient with motional freedom in the three principal directions to allow the focus to be placed anywhere in the human body. Alternatively, the focus can be adjusted electronically by using a more complicated FUS transducer, a so-called phased array FUS transducer, in fact a combination of multiple transducers that can be controlled individually by electronic means thus allowing to move the focus. Acoustic contact between the focus and the FUS transducer is assured using appropriate water, gel, or other means giving an uninterrupted acoustic path from transducer to focus. A Sparc 10 (Sun Microsystems, Mountain View, Calif.) workstation interfaced to the motor controls, the FUS pulse generator and the MR imaging system is used to program, plan, monitor and control therapy. Cline et al., supra, and Zwart et al., supra.

The area of the target is immobilized by gentle straps to the bed. (Note that the more accelerated the procedure, the less the need for immobilization; with very accelerated procedures immobilization is unnecessary.)

Highly detailed MRI images are obtained with a suitable contrast to determine accurately the computer coordinates of the target (e.g. tumor, or ischemic area) as per standard MRI procedures. Based on i) coordinates of the target, ii) estimates of ultrasound attenuation, iii) acoustic impedance transitions in the ultrasound paths, the focus, power and exposure time of the FUS device are targeted to give an increase in temperature of three degrees Celsius in approximately 10 seconds at the target.

The FUS device is switched on for 10 seconds. Immediately following the FUS exposure, a rapid MRI temperature image is taken as per the procedure outlined in J. de Zwart et al. (1996), *J. Magn. Reson.* Series B, 112:86–90 and references therein). An evaluation is made as to the following criteria: i) Does the heated spot correspond with the target (comparison of anatomical MRI and temperature MRI), and ii) Is the temperature elevation indeed 3 degrees Celsius (quantification of temperature, see J. de Zwart et al. under 5)? If not, the FUS target is moved in the first case, and the power is adjusted in the second case. The trial heating is repeated until location and power correspond with the target. Note that, since hsp-70B promoter activity is linearly proportional with the duration, gene expression in this adjustment procedure is limited because of its short duration.

Once power and focus have been adjusted, the therapeutic dose of the ultrasound is delivered. For the hsp-70B promoter, an elevation by 3 degrees for 15 minutes gives rise to very large expression of the gene under hsp-70B control. Therefore, the initial exposure is 15 minutes. It can be increased or decreased at the discretion of the attending physician, taking into consideration the severity of the condition treated, the condition (age, health) of the patient, and the size and location of the target area.

The patient is then removed from the MRI. Evaluation of therapy is performed by clinical examination and regular follow-up of detailed anatomical MRI to evaluate tumor shrinkage.

Example 2

Example 2 is performed using the methods described in Example 1, except that the gene for vascular endothelial growth factor (VEGF) is transferred into cells of tissues suffering from ischemic damage. The adenoviral vector that contains the VEGF gene is injected directly into the vicinity of the affected tissue and or into blood vessels that directly feed into the affected tissues. Gene expression is induced and monitored as described above. Evaluation of therapy is by clinical examination and regular follow-up of detailed anatomical MRI to evaluate healing of ischemic tissue.

Example 3

Example 3 describes the use of focused ultrasound (FUS) guided by MRI to heat a predetermined area of the thigh muscle and activate endogenous heat shock genes in a rat model.

Harlan Sprague-Dawley rats (n=6) with a mass of 428±48 g were studied under an approved National Institutes of Health animal protocol. The relatively large size of the rat ensures that the ultrasound will focus deep within the biceps femoris muscle in the rat's right hind leg.

A polycarbonate rat holder was constructed that contained both the FUS transducer and an MR surface coil. The holder was placed in a fiberglass tube that was partially filled with water. The ultrasound passes through a 38 mm aperture in the platform supporting the animal.

The holder was inclined to insure that the rat hind leg was underwater while maintaining its head at a safe level above the water. The leg was supported by four 2-0 braided polyester fiber sutures forming a grid across the aperture. The FUS transducer was positioned so that the focus was 5 mm into the rat thigh.

Earlier tests with high intensity FUS performed on rats and on fresh chicken legs had indicated that focusing close to the skin may cause burns to the skin. The rat was anesthetized with an intraperitoneal administration of ketamine and xylazine. Three additional steps were taken to minimize the reflection and disruption of the ultrasound caused by acoustic impedance mismatches at interfaces. First, the right leg was shaved front and back with electric shears. Shaving also helped to reduce potential sources of RNA degradation in the harvesting of the tissue. The skin was then cleaned with alcohol swabs and wet with a surfactant to reduce the retention of air microbubbles along the skin. Finally, after the rat had been immersed in water, large air bubbles trapped under the leg were released. The rat was securely positioned on its right side on the platform, and care was taken to insure that the focal region of the ultrasound was not close to any bones in the leg. Respiration was monitored to maintain a proper level of sedation. Body temperature was measured rectally with a pair of fiber optic temperature probes (Luxtron Fluoroptic Model SMM, Santa Clara, Calif.). Another pair of probes monitored the temperature of the water bath. The bath temperature was controlled by heat exchange with a recirculating water heater. The target rectal temperature was 37 to 38° C. Deionized water was used for the bath because it was free of microbubbles that could interfere with the ultrasound.

Transmitting the ultrasound directly through water to the leg was found to be more effective than other methods that used a combination of ultrasound gel and water contained in a balloon or condom. The FUS transducer (Specialty Engineering Associates, Soquel, Calif.) was 38 mm in diameter with a radius of curvature and nominal focal length of 25 mm. Its resonance frequency was 1.459 MHz. The predicted focal region, based on geometry and defined as the full-width-half-maximum intensity area (Bamber JC, Tristam M., "Diagnostic Ultrasound". In: Webb S, ed. THE PHYSICS OF MEDICAL IMAGING. Bristol: Adam Hilger, 1988; 328–334), was an ellipsoid with a major axis of 6 mm oriented along the transducer axis and a minor axis of 1 mm. The rf surface coil was potted with epoxy in a 58 mm diameter channel cut in the platform around the FUS aperture. Tuning and matching capacitors were housed out of the water above the rat.

Experiments were performed on a 4.7 T magnet controlled with an Inova console (Varian NMR Instruments, Palo Alto, Calif.). MR temperature mapping was performed using rf spoiled gradient echo imaging (de Poorter et al. (1995), "Noninvasive MRI thermometry with the proton resonance frequency (PRF) method: in vivo results in human muscle", *Magn. Reson. Med.* 33:74–81 (1996); de Zwart et al., "Fast magnetic-resonance temperature imaging." *J. Magn. Reson.* B 112: 86–90). The gradient echo data allowed phase difference maps to be reconstructed. The hydrogen nuclei in water demonstrate a temperature dependent chemical shift that allows one to calculate temperature changes from these phase differences. Echo and repetition times were 12 and 75 ms, respectively. Five slices with a thickness of 2 mm and a spacing of 3.5 mm were acquired sequentially in an interleaved fashion. They were initially centered around the nominal focal point. 128×128 maps were calculated for the 10×10 cm$^2$ field of view. Temperature resolution was approximately 0.15° C.

An initial "cold" reference image was acquired once the rat was properly positioned in the magnet and its temperature stabilized in the target range. This image was used to calculate temperature changes in subsequent maps. Then, the ultrasound was turned on at a low level (~1 W electric) just long enough to acquire a set of five slices. Data was exported to a Sun workstation where user-written IDL code was used to construct temperature maps (see also ref. 7). From the maps, the focal region was identified. If necessary, adjustments to the slice locations were made to center the focus in one slice. Heating of the leg muscle by continuous FUS then occurred for 45 minutes. Real-time temperature maps were used to keep the focal region elevated by 8° C. at its center, giving about a 5° C. rise at the edge of the region.

Thus, the focal region was heated to 42–45° C. Expression of the hsp70 gene continued for an additional 45 minutes after the heating period while MRI monitored the leg temperature.

Throughout the experiment the rat's core body temperature as measured by the rectal probes was maintained within one degree of the target range, and respiration was monitored to insure proper anesthesia.

The rat was euthanized with pentobarbital and the right leg muscle was frozen using a freeze clamp cooled in liquid nitrogen (−196° C.). The frozen sample was transported in a sterile specimen jar immersed in liquid nitrogen to a lab where the tissue samples were prepared for analysis. The samples were taken from a three-by-three grid centered on the nominal axis of the FUS beam. The center sample was subdivided by depth into three giving a total of eleven samples. The size of each muscle sample was approximately 4 mm×4 mm×2 mm.

The samples were kept frozen until they were placed in Eppendorf tubes containing 0.5 ml Trizol solution (Life Technologies, Gaithersburg, Md.) and homogenized. The solution and homogenized tissue were then stored at −80° C. until RNA was extracted. The RNA (30 µg sample per lane) was separated by gel electrophoresis, and transferred to a nylon membrane. The integrity of the mRNA was assessed by visualization of the ethidium bromide-stained RNA following transfer. The membranes were hybridized with a $^{32}$p-labeled cDNA that is complementary to the inducible hsp70 mRNA. Autoradiographs were created and analyzed for amount of inducible hsp70 in each sample.

Figure 5A:
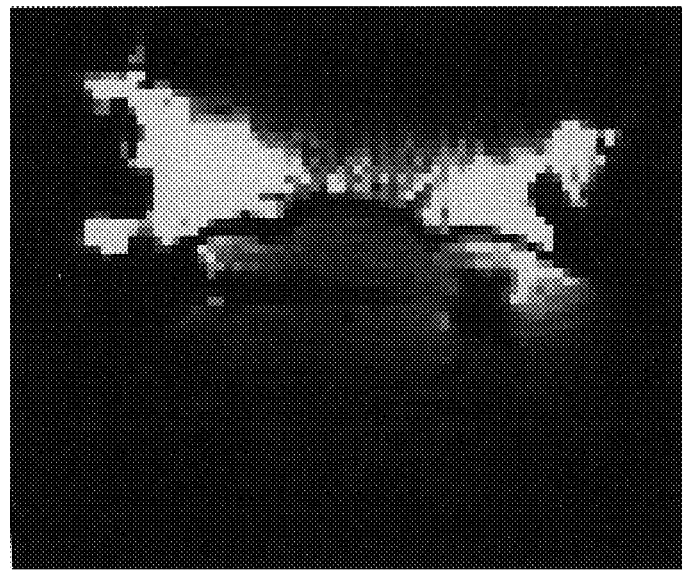
FIG. 5(*a*) is an intensity image of the rat leg in the focal plane showing, from bottom to top, the transducer (in part), the water bath with a high signal intensity (in the middle the inclined table with the aperture for FUS can be seen), and finally the rat leg.
Figure 5B:
Figure 5C:

An intensity image of the slice containing the focal region is shown in FIG. 5(a). FIG. 5(b) shows the temperature change in the same slice of the rat leg after one minute of heating. The field of view is identical to FIG. 5(a), but temperatures were calculated in a smaller region of interest only. In addition, pixels falling below a threshold intensity were not calculated because of poor signal-to-noise and appear black. Since there has been little diffusion of heat into the surrounding tissue, FIG. 5(b) serves as a good indicator of the size of the focal region. FIG. 5(c) is a temperature map acquired after about three minutes of heating. Thermal diffusion is apparent, and subsequent data showed that an approximately steady state had been reached.

Figure 6:
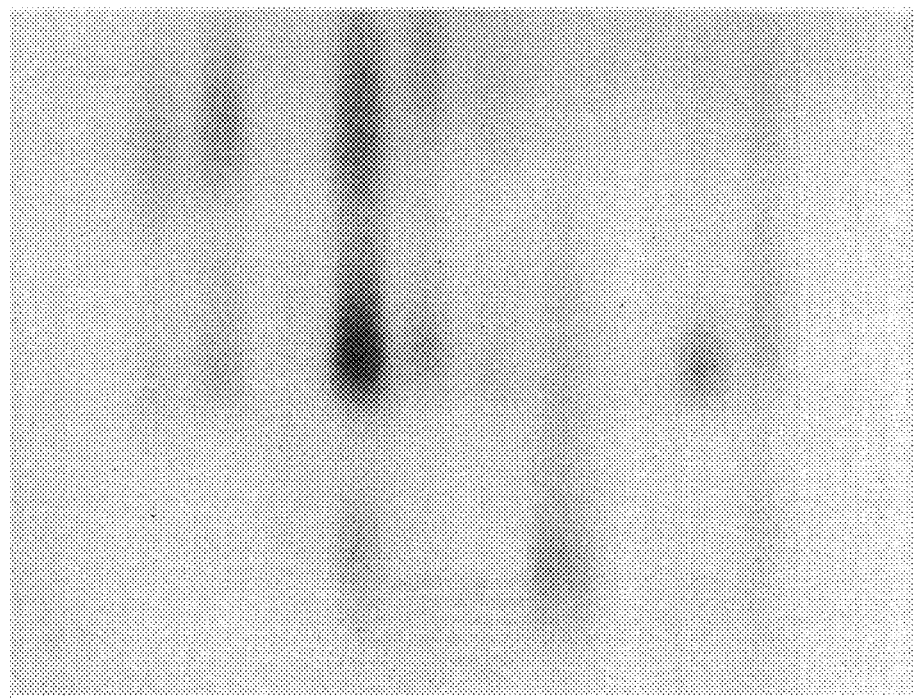
FIG. 6 shows the results of a Northern blot of locally heated rat leg. Lanes 5, 6, and 7 are of samples taken from the ultrasound focal region. Lane 5 shows markedly higher expression of RNA at about 2.3 kb (arrow). Differential expression between this sample and the surrounding samples ranges from a factor of 3 to 67.

FIG. 6 shows the Northern blot of total RNA prepared from rat thigh muscle following exposure to MRI-guided FUS and reacted with random primed labeled human hsp70 stress inducible gene probe. The probe hybridizes strongly in lane 5 at a position of about 2.3 kb (arrow), as expected for a 70,000 dalton protein. RNA loaded into lanes 8 and 11 was somewhat degraded. Measurements show that the differential expression of heat-inducible hsp70 in the focal region ranges from a factor of 3 to 67.

These results demonstrate that low level continuous FUS can be used to elevate the expression of endogenous hsp70 mRNA in vivo, and that the hsp70 promoter is a suitable target for use in control of gene expression based on local heat. The results also show that MRI can provide interactive temperature maps for monitoring local heating of in vivo tissue by FUS. Incorporation of three-dimensional fast imaging methods like PRESTO should allow for faster temperature maps.

Example 4

Example 4 describes the use of focused ultrasound (FUS) guided by MRI to heat a predetermined area of the thigh muscle and activate endogenous heat shock genes in a mouse whose muscle tissue has been transformed with an adenoviral vector.

A transgenic mouse which contains a genetically engineered LacZ gene under control of the hsp70 promoter (For methods of making transgenic mice, see, e.g., Charron et al. (1995) *J. Biol. Chem.* 270: 30604–10; for adenoviral vectors useful in transforming cells, see Addison et al. (1995) *Proc. Nat. Acad. Sci. U.S.A.* 92: 8522–6 and Wang et al. (1996) *Proc. Nat. Acad. Sci. U.S.A.* 93: 3932–6) is treated as described in Example 3 (i.e., regions of the thigh muscle having preselected coordinates are heated using FUS-MRI). A significant increase the desired gene transcripts in the FUS focal spot is observed.

All publications, patents and patent applications mentioned in this specification are hereby incorporated by reference for all purposes, to the same extent as if each individual publication, patent or patent application had been specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for the spatial and temporal control of the expression of a genetically engineered gene of interest operably linked to a human hsp-70B promoter in host cells within a preselected region of a human, comprising:
    selectively heating said region by focused ultrasound;
    monitoring the temperature distribution of said region by MRI temperature imaging; and
        adjusting said heating according to said monitoring so as to provide a 3° C. increase in the temperature at the center of said region;
    thereby spatially and temporally controlling the expression of said gene of interest.

2. The method of claim 1, wherein the gene of interest is selected from the group consisting of LacZ or chloramphenicol acetyltransferase.

3. A method of claim 1, wherein the temperature increase is initially maintained by said heating for about 15 minutes.

4. The method of claim 1, wherein the temperature increase is imaged with a spatial resolution of 3–4 mm diameter and a temperature resolution of 20°C.

5. The method of claim 1, wherein the gene of interest encodes a human lymphokine.

6. The method of claim 1, wherein the gene of interest encodes a VEGF.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 108 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: -
      (B) LOCATION: 1..108
      (D) OTHER INFORMATION: /note= "minimal Drosophila heat shock
         protein (hsp70) promoter containing heat
         shock element (HSE) HSEII, HSEI, GAGA
         and TATA elements"

(xi) SEQUENCE DESCRIPTION: SEQ ID NO: 1:

GCTCTCGTTG GTTCGAGAGA GCGCGCCTCG AATGTTCGCG AAAAGAGCGC CGGAGTATAA      60

ATAGAGGCGC TTCGTCTACG GAGCGACAAT TCAATTCAAA CAAGCAAA                  108

(2) INFORMATION FOR SEQ ID NO: 2:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..18
        (D) OTHER INFORMATION: /note= "heat shock element II (HSEII)"

(xi) SEQUENCE DESCRIPTION: SEQ ID NO: 2:

CTCTCGTTGG TTCGAGAG                                                    18

(2) INFORMATION FOR SEQ ID NO: 3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..18
        (D) OTHER INFORMATION: /note= "heat shock element I (HSEI)"

(xi) SEQUENCE DESCRIPTION: SEQ ID NO: 3:

GCCTCGAATG TTCGCGAA                                                    18

(2) INFORMATION FOR SEQ ID NO: 4:

(i) SEQUENCE CHARACTERISTICS:
        (A) LENGTH: 286 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..286
        (D) OTHER INFORMATION: /note= "human heat shock protein
            (hsp70B) promoter"

(xi) SEQUENCE DESCRIPTION: SEQ ID NO: 4:

GCGTCCTCAG AGCCAGCCGG GAGGAGCTAG AACCTTCCCC GCGTTTCTTT CAGCAGCCCT      60

GAGTCAGAGG CGGGCTGGCC TTGCAAGTAG CCGCCCAGCC TTCTTCGGTC TCACGGACCG     120

ATCCGCCCGA ACCTTCTCCC GGGGTCAGCC CCGCGCTGCG CCGCCCGGCT GACTCAGCCC     180

GGGCGGGCGG GCGGGAGGCT CTCGACTGGG CGGGAAGGTG CGGGAAGGTT CGCGGCGGCG     240

GGGTCGGGGA GGTGCAAAAG GATGAAAAGC CCGTGGACGG AGCTGA                   286

-continued (2) INFORMATION FOR SEQ ID NO: 5:

(i) SEQUENCE CHARACTERISTICS:
        (A) LENGTH: 197 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..197
        (D) OTHER INFORMATION: /note= "human 70 kDa heat shock protein
            (hsp70) promoter"

(xi) SEQUENCE DESCRIPTION: SEQ ID NO: 5:

```
GAAGAGTCTG GAGAGTTCTG AGCAGGGGGC GGCACTCTGG CCTCTATTGG TCCAGGAAGG        60

CTGGGGGGCA GGACGGGAGG CCAAACCCCT GGAATATTCC CGACCTGGCA GCCTCATCGA       120

GGCTCGGTGA TTGGCTCAGA AGGGAAAAGG CGGGTCTCCG TGACGACTTA TAAAACGCCA       180

GGGGCAACGG GTCCGGA                                                     197
```

(2) INFORMATION FOR SEQ ID NO: 6:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

```
NGAANNTTCN                                                              10
```

(2) INFORMATION FOR SEQ ID NO: 7:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

```
NTTCNNGAAN                                                              10
```